United States Patent
Kakuchi et al.

(10) Patent No.: US 12,083,241 B2
(45) Date of Patent: Sep. 10, 2024

(54) TAXI VEHICLE AND TAXI SYSTEM

(71) Applicant: TOYOTA JIDOSHA KABUSHIKI KAISHA, Toyota (JP)

(72) Inventors: Makoto Kakuchi, Toyota (JP); Osamu Izumida, Nagoya (JP); Shunji Inoue, Okazaki (JP); Takumi Hamajima, Takatsuki (JP); Mitsushi Kintaka, Kariya (JP); Toshihiro Andou, Kariya (JP); Masamitsu Takahira, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 248 days.

(21) Appl. No.: 17/649,624

(22) Filed: Feb. 1, 2022

(65) Prior Publication Data

US 2022/0265881 A1   Aug. 25, 2022

(30) Foreign Application Priority Data

Feb. 25, 2021   (JP) ................................. 2021-029056

(51) Int. Cl.
| | |
|---|---|
| *A61L 2/24* | (2006.01) |
| *A61L 2/07* | (2006.01) |
| *A61L 2/10* | (2006.01) |
| *A61L 2/18* | (2006.01) |
| *A61L 2/20* | (2006.01) |
| *B60Q 1/50* | (2006.01) |
| *B60S 1/64* | (2006.01) |
| *B60W 60/00* | (2020.01) |
| *G07B 15/00* | (2011.01) |

(52) U.S. Cl.
CPC .................... *A61L 2/24* (2013.01); *A61L 2/07* (2013.01); *A61L 2/10* (2013.01); *A61L 2/18* (2013.01); *A61L 2/202* (2013.01); *B60S 1/64* (2013.01); *B60W 60/00253* (2020.02); *A61L 2202/14* (2013.01); *A61L 2202/25* (2013.01); *B60Q 1/5037* (2022.05); *G07B 15/00* (2013.01)

(58) Field of Classification Search
None
See application file for complete search history.

(56) References Cited

U.S. PATENT DOCUMENTS

| | | | | |
|---|---|---|---|---|
| 9,971,348 | B1 * | 5/2018 | Canavor | H04W 12/065 |
| 2019/0091738 | A1 * | 3/2019 | Chen | B60H 1/00742 |

(Continued)

FOREIGN PATENT DOCUMENTS

| | | |
|---|---|---|
| JP | S55050147 A | 4/1980 |
| JP | 2007284038 A | 11/2007 |

(Continued)

*Primary Examiner* — Christian Chace
*Assistant Examiner* — Shayne M. Gilbertson
(74) *Attorney, Agent, or Firm* — Dickinson Wright, PLLC

(57) ABSTRACT

A taxi vehicle that autonomously transports a user to a destination with no driver in the vehicle includes a cleaning device and a notification device. The cleaning device is configured to perform cleaning processing for removing at least one of harmful materials and odors from a vehicle cabin after the user has finished using the taxi vehicle. The harmful materials are those harmful to a human body. The notification device is configured to notify a person of the cleaning degree of the vehicle cabin. The person is a person outside the vehicle who wishes to use the vehicle.

9 Claims, 8 Drawing Sheets

(56) References Cited

U.S. PATENT DOCUMENTS

| | | | |
|---|---|---|---|
| 2019/0168711 A1* | 6/2019 | Oesterling | G06F 16/51 |
| 2021/0009150 A1* | 1/2021 | Chen | B60W 50/14 |
| 2021/0322613 A1* | 10/2021 | Lacaze | G06N 20/00 |
| 2022/0118952 A1* | 4/2022 | Gutowski | B60W 10/30 |
| 2022/0185062 A1* | 6/2022 | Khaw | B60H 1/00985 |

FOREIGN PATENT DOCUMENTS

| | | |
|---|---|---|
| JP | 2010234905 A | 10/2010 |
| JP | 2017174208 A | 9/2017 |
| JP | 2019017412 A | 2/2019 |

* cited by examiner

TAXI VEHICLE AND TAXI SYSTEM

CROSS-REFERENCE TO RELATED APPLICATION

This application claims priority to Japanese Patent Application No. 2021-029056 filed on Feb. 25, 2021, incorporated herein by reference in its entirety.

BACKGROUND

1. Field of the Disclosure

This specification discloses a taxi vehicle that transports a user to a destination autonomously with no driver in the taxi vehicle, and a taxi system that includes a plurality of such taxi vehicles.

2. Description of Related Art

An unspecified number of users ride on a taxi vehicle. Therefore, the driver of a taxi vehicle tries to keep the vehicle cabin clean so that any user can feel comfortable in the vehicle cabin. More specifically, the driver of a taxi vehicle tries to keep the vehicle cabin clean as necessary by ventilating or by using air refreshers and sanitizers.

SUMMARY

In the meantime, it has been proposed in recent years to use an autonomous driving vehicle as a taxi vehicle. In this case, there is no driver in the taxi vehicle. Therefore, in an autonomous driving taxi vehicle, a driver cannot keep the vehicle cabin clean.

To address this problem, Japanese Unexamined Patent Application Publication No. 2007-284038 (JP 2007-284038 A) discloses a technique in which a smoking sensor is equipped in the vehicle for detecting smoking and, when smoking is detected, the air conditioner is operated in the outside air circulation mode for ventilation. However, the technique disclosed in JP 2007-284038 A simply ventilates automatically when smoking is detected but cannot clean the vehicle cabin before the user rides on the vehicle. In addition, according to the technique disclosed in JP 2007-284038 A, there is no way for the user to know, before riding on the vehicle, whether the vehicle cabin is clean. As a result, according to the conventional technique, there is a possibility that the user cannot reliably use an autonomous driving taxi vehicle.

In view of the foregoing, this specification discloses a taxi vehicle and a taxi system that the user can use it more reliably.

A taxi vehicle disclosed in this specification is a taxi vehicle that autonomously transports a user to a destination with no driver in the vehicle. The taxi vehicle includes a cleaning device and a notification device. The cleaning device is configured to perform cleaning processing for removing at least one of harmful materials and odors from the vehicle cabin after the user has finished using the taxi vehicle. The harmful materials are those harmful to the human body. The notification device is configured to notify a person of the cleaning degree of the vehicle cabin. The person is a person outside the vehicle who wishes to use the vehicle.

This configuration makes it possible to keep the taxi vehicle clean. In addition, this configuration provides the user with the information on the cleaning degree of the taxi vehicle before the user rides on it, allowing the user to more reliably use the taxi vehicle.

The cleaning processing described above may include sanitization processing that outputs at least one of disinfectants and cleaning energy to the vehicle cabin for sanitization.

The sanitization processing performed as described above significantly reduces the health risk of the user.

The taxi vehicle described above may further include a presence sensor configured to detect whether a person or a piece of baggage is still present in the vehicle cabin. The cleaning device is configured not to perform the sanitization processing during the period while the presence sensor detects that at least one of the person and the baggage is still present in the vehicle cabin.

This configuration makes it possible to perform the sanitization processing with a person or a piece of baggage not present in the vehicle cabin. As a result, this configuration allows a high-concentration disinfectant or high-power cleaning energy to be used for the sanitization processing, allowing disinfection to be performed more reliably and quickly.

In addition, the taxi vehicle may further include a payment device configured to be used for paying the usage fare of the taxi vehicle. When the user starts using the taxi vehicle, the cleaning device may be configured to finish the sanitization processing even before the sanitization processing is completed. In addition, the payment device may be configured to change the usage fare according to the cleaning degree at the time when the user starts using the taxi vehicle.

This configuration allows the user in a hurry to start using the taxi vehicle immediately. In addition, this configuration makes the taxi vehicle available for use before disinfection is completed, leading to a reduction in the waiting time of the taxi vehicle and to an improvement in the profitability of the taxi vehicle.

The notification device may include at least one of a light, a display, a projector, a speaker, and a communication device. The light is installed at a position that is on the taxi vehicle and is visible from outside of the taxi vehicle. The display is configured to display an image in the display area that is provided at a position on the taxi vehicle and is visible from outside of the taxi vehicle. The projector is configured to project an image on the road surface around the taxi vehicle. The speaker is configured to output a voice to the outside of the vehicle. The communication device is configured to send information to an information terminal outside the vehicle.

This configuration makes it possible for the user who wishes to use the taxi vehicle to reliably recognize the cleaning degree of the taxi vehicle before riding on it.

A taxi system disclosed in this specification may be a taxi system including a plurality of the taxi vehicles. The taxi vehicles may be divided into smoking vehicles in which smoking is permitted and non-smoking vehicles in which smoking is prohibited. The notification device may be configured to output the cleaning degree and, in addition, whether smoking is permitted.

This configuration makes it possible for both smokers and non-smokers to selectively use taxi vehicles, allowing both smokers and non-smokers to use the taxi vehicle more comfortably.

According to the technique disclosed in this specification, the user can use a taxi vehicle more reliably.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Figure 1:
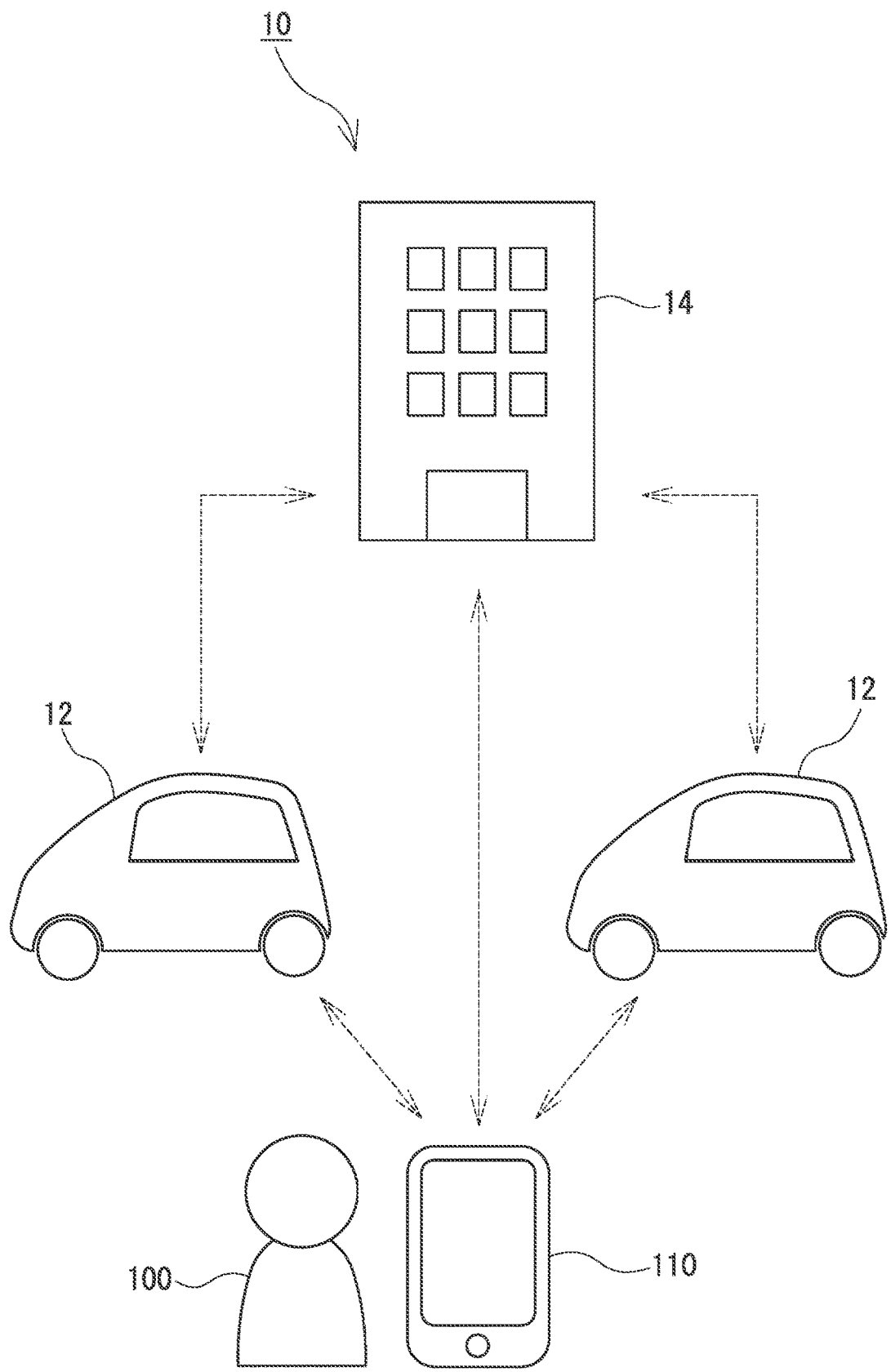
FIG. 1 is an image diagram showing a configuration of a taxi system.

A configuration of a taxi system 10 will be described below with reference to the drawings. FIG. 1 is an image diagram showing a configuration of the taxi system 10. The taxi system 10 includes a plurality of taxi vehicles 12 and a management device 14.

The taxi vehicle 12 is a vehicle that receives a request from a user and transports the user to a desired destination. The taxi vehicle 12 in this example is a single-seater vehicle with a capacity of one person. As a matter of course, an infant is not counted as an occupant and can be carried with an adult. The taxi vehicle 12 is an autonomous driving vehicle in which the vehicle performs all dynamic driving tasks. This means that the taxi vehicle 12 has no driver in the vehicle.

"Autonomous driving" described above means that the vehicle performs almost all of the dynamic driving tasks; for example, autonomous driving level of one of Level 3 to Level 5 defined by the American Society of Automotive Techniques (SAE). Level 3 is a driving mode in which all dynamic driving tasks are automated in a specific place such as a highway, but a driver's operation is required in an emergency. Level 4 is a driving mode in which all dynamic driving tasks are automated only in a specific place, and an operation in an emergency is also automatically processed. Level 5 is a driving mode in which autonomous driving is possible under almost all conditions and in all places. Level 5 means the so-called "complete autonomous driving."

The management device 14 manages the dispatch of the taxi vehicles 12. The management device 14 collects the information on the location and the operation status of each of the taxi vehicles 12 and manages the collected information. The operation status of the taxi vehicle 12 includes the states, for example, free, in-service, out-of-service, hired, and cleaning. The management device 14 also collects the information on the cleaning level that indicates the cleaning degree of the vehicle cabin of each of the taxi vehicles 12. The cleaning level will be described later. In addition, with consideration for the requests from users and for the distribution of taxi vehicles 12 and people in the city, the management device 14 calculates a desired arrangement of the taxi vehicles 12 and, based on this calculation, outputs dispatch instructions to the taxi vehicles 12. The taxi vehicle 12 will travel to a location as appropriate in accordance with this vehicle dispatch instruction.

There are three usage modes of the taxi vehicle 12: (1) a booking usage mode in which the usage date and time of the taxi vehicle 12 is specified, (2) a calling usage mode in which a user 100 makes a call for a taxi and uses the taxi vehicle 12, and (3) a pickup usage mode in which the user 100 moves to a place where the taxi vehicle 12 is located and starts using it. First, the booking usage mode will be described. For the booking usage mode, the user 100 operates an information terminal (referred to as "user terminal 110" in the description below) managed by the user 100 himself/herself to send a booking request to the management device 14. The booking request includes at least the riding date/time and the riding position desired by the user. In accordance with this booking request, the management device 14 dispatches the taxi vehicle 12 to the specified place at the specified date/time.

Figure 2:
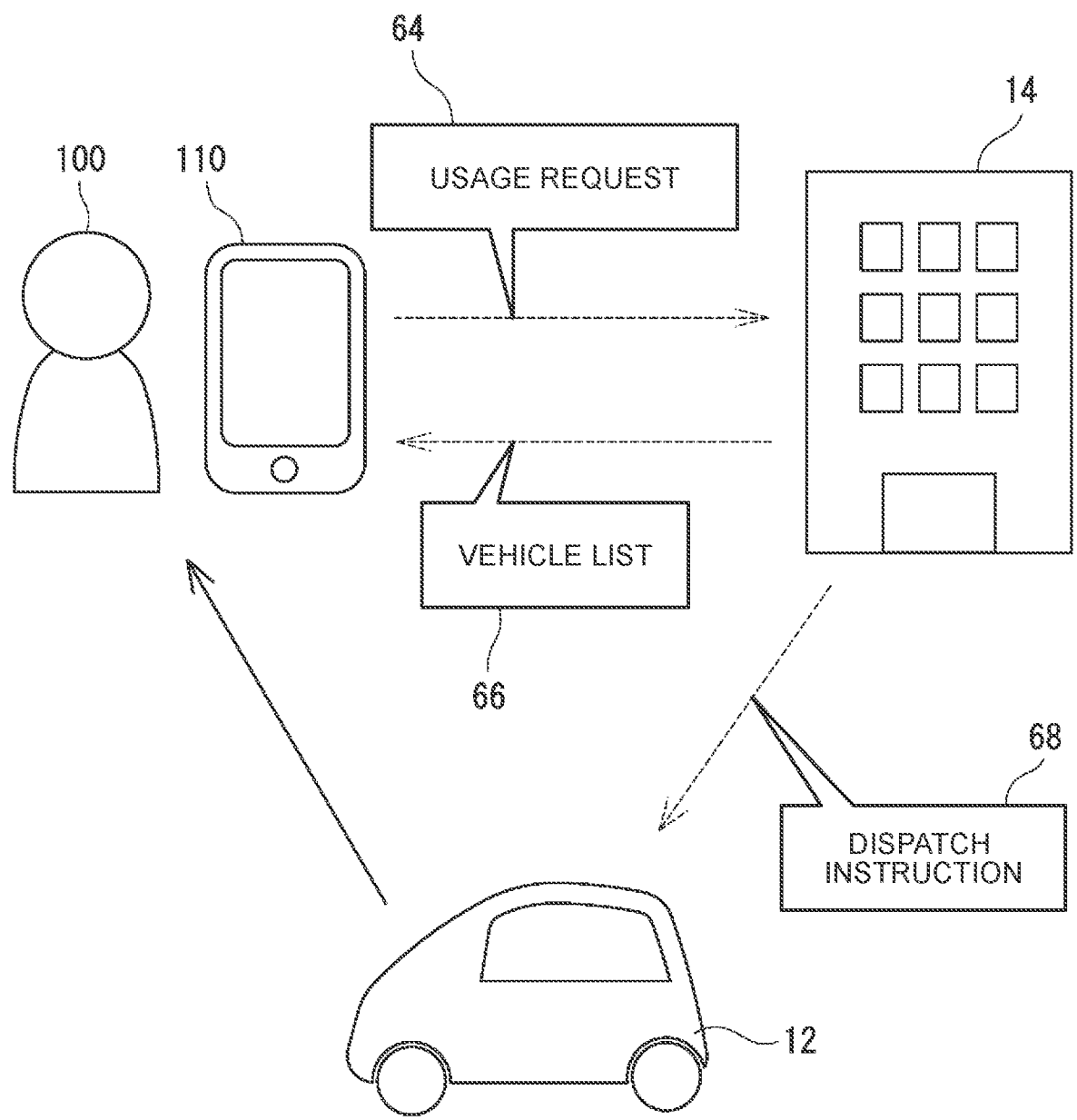
FIG. 2 is an image diagram showing calling usage.

Next, the calling usage mode will be described. FIG. 2 is an image diagram showing the calling usage mode. In the calling usage mode, the user 100 operates the user terminal 110 to send a usage request 64 to the management device 14. The usage request 64 includes at least the position information on the user 100. The usage request 64 may further include at least one of the destination, the payment method, the number of the taxi vehicles 12 to be used, and other requirements (for example, the air conditioning condition of the taxi vehicle 12).

Upon receiving the usage request 64, the management device 14 sends a vehicle list 66 to the user terminal 110. The vehicle list 66 is a list of the taxi vehicles 12 available to the user 100, that is, a list of the taxi vehicles 12 that can move to the position of the user 100 within a predetermined time. From a plurality of taxi vehicles 12 recorded in the vehicle list 66, the user 100 selects the taxi vehicle 12 to be used. To aid in this selection, the vehicle list 66 may further include, for each the taxi vehicles 12, an estimated time required to reach the position of user 100, the cleaning level of the taxi vehicle 12, etc. In any case, when the user 100 selects the taxi vehicle 12 to be used, the management device 14 sends a dispatch instruction 68 to the selected the taxi vehicle 12. Upon receiving this dispatch instruction 68, the taxi vehicle 12 moves to the current position of the user 100 autonomously.

Figure 3:
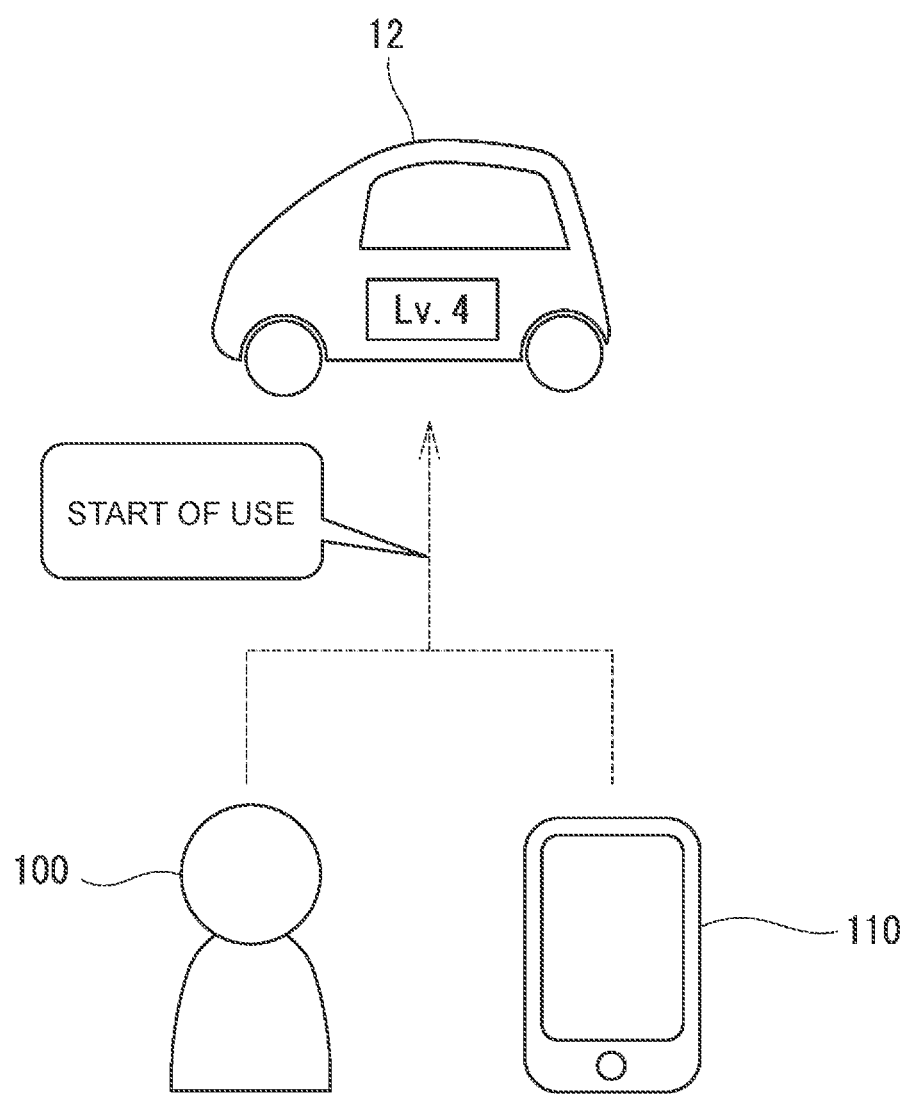
FIG. 3 is an image diagram showing pickup usage.

Next, the pickup usage mode will be described. FIG. 3 is an image diagram showing the pickup usage mode. In the pickup usage mode, the user 100 moves to a place where the taxi vehicle 12 in the free state is located and notifies the taxi vehicle 12 of the start of the use of the taxi vehicle 12. The start-of-use notification may be entered by operating the user terminal 110 or by operating the user interface device (referred to as "user I/F" in the description below) mounted on the taxi vehicle 12. More specifically, the user 100 may operate the user terminal 110 to send the data indicating the start-of-use to the taxi vehicle 12. The user 100 may also get in the taxi vehicle 12 and operate the user I/F (for example, a touch panel or the like) mounted on the taxi vehicle 12 to notify the taxi vehicle 12 of the start of use. Upon receiving the start-of-use notification, the taxi vehicle 12 notifies the management device 14 that the transportation of the user 100 has started, that is, the vehicle has entered the in-service state.

In any of the booking usage mode, calling usage mode, and pickup usage mode, the user 100 notifies the taxi vehicle 12 of end of use when the taxi vehicle 12 has reached the destination. When the end-of-use notification is received, the usage fare of the taxi vehicle 12 is paid. After payment, the taxi vehicle 12 moves to the next destination according to the dispatch instruction 68 received from the management device 14. When the use by the user 100 is finished, the taxi vehicle 12 starts cleaning processing for removing harmful materials and/or odors from the vehicle. The details of this cleaning processing will be described later.

Figure 4:
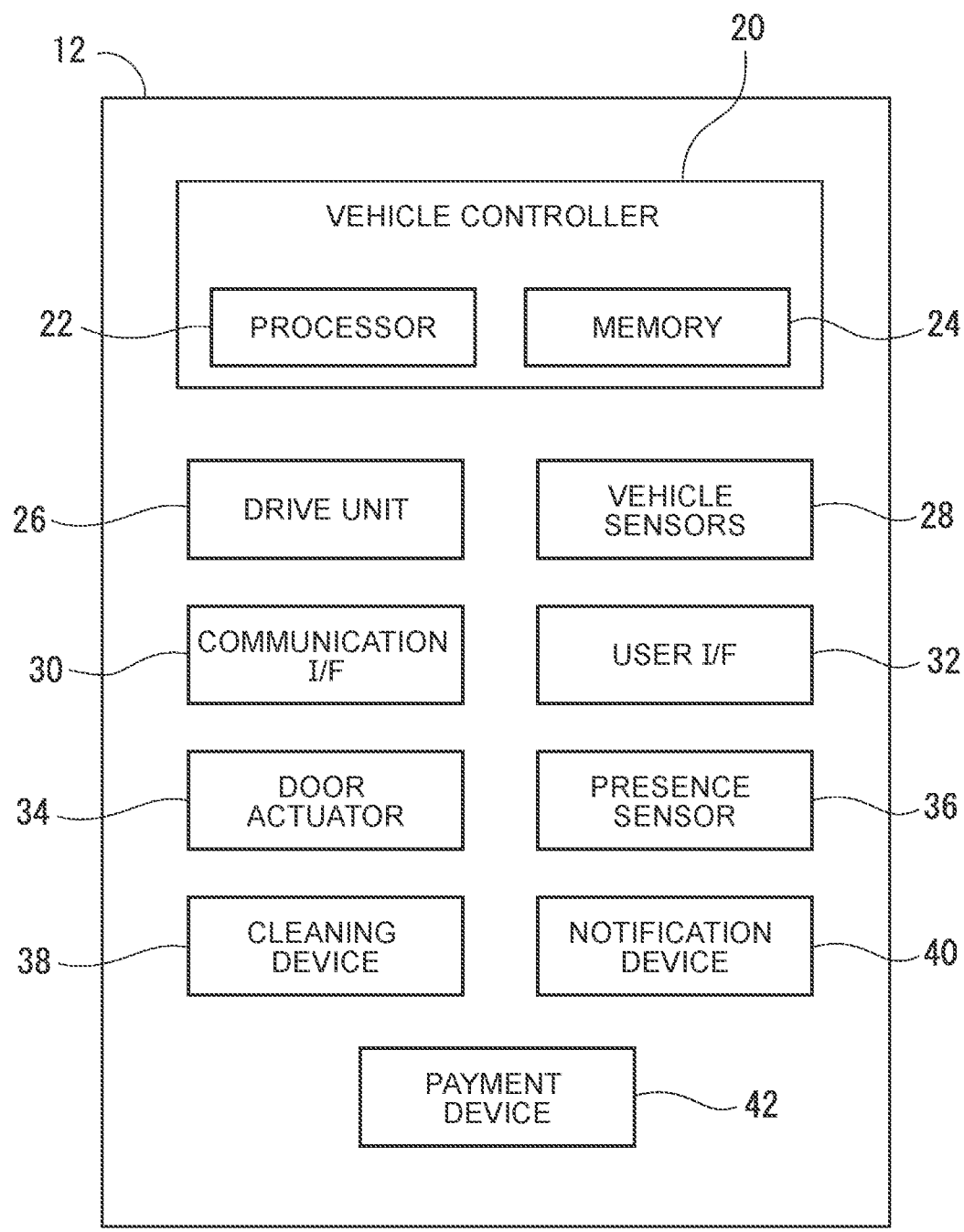
FIG. 4 is a block diagram showing a configuration of a taxi vehicle.

Next, the configuration of each of the taxi vehicle 12 and the management device 14 will be described below. FIG. 4 is a block diagram showing the configuration of the taxi vehicle 12. A drive unit 26, a device that generates a mechanical action for driving the taxi vehicle 12, includes, for example, a motor, a power transmission device, a brake device, a suspension device, a steering device, and the like. Vehicle sensors 28 include a plurality of sensors for sensing various types of information necessary for the traveling of the taxi vehicle 12. The vehicle sensors 28 include, for example, sensors for detecting the surrounding environment of the taxi vehicle 12 (for example, a camera, LiDAR, a millimeter wave radar, an ultrasonic sensor, etc.), sensors for detecting the current position of the taxi vehicle 12 (for example, GPS, etc.), and sensors for detecting the traveling state of the taxi vehicle 12 (for example, acceleration sensor, gyro sensor, etc.). The information detected by the vehicle sensors 28 is sent to a vehicle controller 20. The vehicle controller 20 calculates the acceleration/deceleration amount and the steering amount of the taxi vehicle 12 based on the information detected by the vehicle sensors 28 and, based on the calculated amount, drives the drive unit 26.

A communication I/F 30 uses a communication technique to communicate with the information devices outside the vehicle. In this case, the information devices with which to communicate include, for example, the management device 14, the user terminal 110, and other the taxi vehicles 12. Such communication may be carried out using mobile data communication provided by a mobile phone company, using short-range wireless communication such as Bluetooth (registered trademark), or using a dedicated communication line.

A user I/F 32 is a device that presents information to the user 100 and, at the same time, accepts an operation from the user 100. The user I/F 32 has, for example, an output device that outputs information to the user 100 and an input device that accepts an operation from the user 100. The output device may include, for example, at least one of a display, a speaker, and a lamp. The input device may include, for example, at least one of a touch panel, a keyboard, a switch, a lever, a pedal, and a microphone.

A door actuator 34 is an actuator that opens and closes the door of the taxi vehicle 12. The door of the taxi vehicle 12 is automatically opened and closed by this door actuator. Therefore, the user 100 does not need to touch the door of the taxi vehicle 12 when getting in and out of the vehicle.

A presence sensor 36 is a sensor that detects whether a person or a piece of baggage is still present in the vehicle. The presence sensor 36 may be, for example, a weight sensor that detects the weight of the vehicle. In this case, when the detected weight is heavier than the vehicle weight in the initial state in which there is no person or baggage in the vehicle, the vehicle controller 20 determines that a person or a piece of baggage is still present. In another form, the presence sensor 36 may be a camera that captures the vehicle cabin. In this case, the vehicle controller 20 determines the presence or absence of a person or a piece of baggage by analyzing the captured image. In still another form, the presence sensor 36 may be a concavo-convex sensor that detects the concavo-convexness of objects based on the reflected wave obtained when sending a radio wave (for example, infrared ray or the like) or an ultrasonic wave. In this case, when the concavo-convex state in the vehicle is different from the initial state stored in advance, the presence sensor 36 determines that there is still a person or a piece of baggage in the vehicle cabin. In any case, the vehicle controller 20 determines whether to perform the cleaning processing, particularly the sanitization processing, according to the detection result of the presence sensor 36.

A cleaning device 38 is a device that performs cleaning processing for cleaning the vehicle cabin. Cleaning means removing at least one of harmful materials, which are harmful to the human body, and odors from the vehicle cabin. A specific configuration of the cleaning device 38 will be described later.

A notification device 40 is a device that notifies persons outside the vehicle who wish to use the taxi vehicle 12 about the cleaning level of the taxi vehicle 12. Those who receive this notification and wish to use the taxi vehicle 12 may be (1) those who are near the taxi vehicle 12, that is, those who are trying to pick up the taxi vehicle 12 in the pickup usage mode or (2) those who are away from the taxi vehicle 12, that is, those who are trying to call the taxi vehicle 12 in the calling usage mode. A specific configuration of the notification device 40 will also be described later.

A payment device 42 is a device used to make payment of the usage fare of the taxi vehicle 12. The form of payment, which is not particularly limited, may include at least one of cash payment, prepaid card payment, automatic withdrawal payment, credit card payment, and barcode payment. To support these forms of payment, the payment device 42 may have a money device that counts the amount of inserted cash and pays changes as needed, a card reader, an RFID reader, a bar code reader, or the like.

The vehicle controller 20 controls the drive of the taxi vehicle 12. For example, the vehicle controller 20 recognizes the surrounding environment of the taxi vehicle 12 using the detection result of the vehicle sensors 28 and, based on the recognized surrounding environment, controls the drive of the drive unit 26 so that the taxi vehicle 12 can drive safely. In addition, the vehicle controller 20 drives the cleaning device 38 to clean the vehicle cabin as necessary.

The vehicle controller 20 described above is physically a computer having a processor 22 and a memory 24. This "computer" also includes a microcontroller that incorporates the computer system into one integrated circuit. The processor 22, which refers to a processor in a broad sense, includes a general-purpose processor (for example, CPU: central processing unit, etc.) and a dedicated processor (for example, GPU: graphics processing unit, ASIC: application specific integrated circuit, FPGA: field programmable gate array, programmable logic device, etc.). The processor 22 does not have to be one physical element; that is, the processor 22 may include a plurality of processors that are physically separated from each other. Similarly, the memory 24 does not have to be one physical element; that is, the memory 24 may be composed of a plurality of memories that are physically separated from each other. The memory 24 may include at least one of a semiconductor memory (for example, RAM, ROM, solid state drive, etc.) and a magnetic disk (for example, a hard disk drive, etc.).

Figure 5:
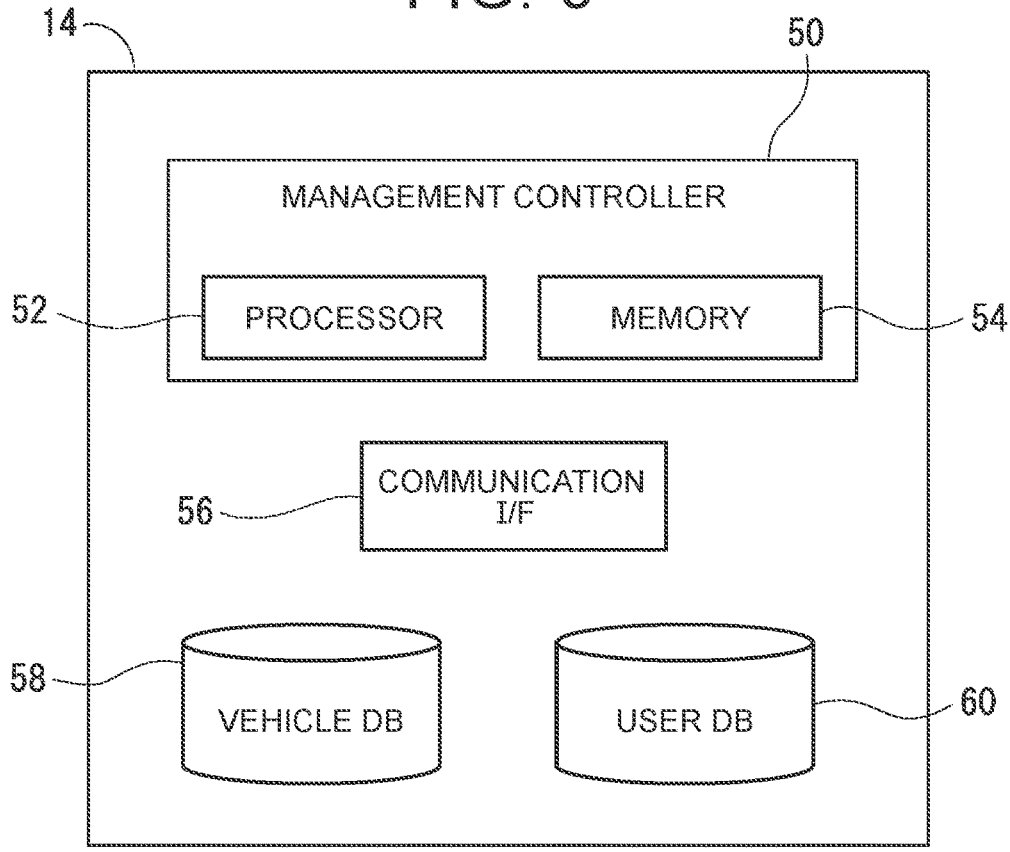
FIG. 5 is a block diagram showing a configuration of a management device.

Next, the configuration of the management device 14 will be described. FIG. 5 is a block diagram showing the configuration of the management device 14. The management device 14 includes a management controller 50, a communication I/F 56, a vehicle DB 58, and a user DB 60. The communication I/F 56 communicates with the user terminal 110 via a general-purpose communication network, such as a mobile data communication network. In addition, the communication I/F 56 communicates with the taxi vehicles 12 via a general-purpose communication network or a dedicated communication network.

The vehicle DB 58 is a database in which the information on the taxi vehicles 12 that make up the taxi system 10 is recorded. The identification information, the position information, the operation status information, and the cleaning level information on each of the taxi vehicles 12 are recorded in the vehicle DB 58.

The information on the users 100 is recorded in the user DB 60. The information on each of the users 100 recorded in the user DB 60 includes, for example, the identification information on the user 100 and the information on the name, payment method, and contact address/number of the user 100. In addition, a place that the user 100 frequently sets as the destination, for example, the address of the home or the address of the company where the user works, may be recorded in association with the identification information on the user 100.

The management controller 50 controls the dispatch of the taxi vehicle 12 in response to a request from user 100 sent from the user terminal 110. In addition, the management controller 50 updates the vehicle DB 58 based on the information sent from the taxi vehicle 12. The management controller 50 also updates the user DB 60 based on the registration information on the user 100 sent from the user terminal 110. The management controller 50 is also configured by a computer having a processor 52 and a memory 54.

Next, the configuration of the cleaning device 38 installed in the taxi vehicle 12 will be described in detail. The cleaning device 38 is a device that cleans the vehicle cabin. As described above, cleaning means removing at least one of harmful materials and odors from the vehicle cabin. Examples of harmful materials include bacteria and viruses that cause infectious diseases, allergens that cause allergies, and other organic materials and chemical materials that adversely affect health.

To remove these harmful materials, the cleaning device 38 may have a sanitizing device that detoxifies harmful materials using cleaning energy or disinfectants. In this case, as the cleaning energy, the sanitizing device may output ultraviolet rays (for example, ultraviolet rays C having a wavelength of 200 nm to 280 nm) or heat. When applying ultraviolet rays, an electric shade may be provided on the windows to prevent ultraviolet rays from leaking to the outside of the vehicle and, during the ultraviolet ray application time, the windows may be covered with the electric shade. When outputting heat, the sanitizing device may heat an object to be sanitized itself or may supply a heat medium (for example, hot water, steam, etc.) to an object to be sanitized. In addition, as the disinfectants, the sanitizing device may output at least one of ozone, ethanol, chlorine sanitizers, and surfactants. Such disinfectants may be output as a gas or as a liquid. Normally, cleaning energy and disinfectants, which detoxify harmful materials, also have an effect of deodorizing some of odor-emitting materials. Therefore, in many cases, sanitizing with the use of a sanitizing device also achieves a deodorizing effect.

The sanitizing device may be a surface sanitizing device that sanitizes the surface of an object in the vehicle cabin or may be a space sanitizing device that sanitizes the entire space of the vehicle cabin. The surface sanitizing device may include, for example, a UV lamp that emits ultraviolet rays, a steamer that injects steam, a disinfectant nozzle that ejects a liquid disinfectant, and the like. The steam injected by the steamer may be saturated steam generated by boiling a liquid or may be superheated steam obtained by further heating saturated steam. Although such a surface sanitizing device is very effective as a countermeasure against infectious diseases, the sanitizing part is limited to the surface of an object. Since the sanitizing part is limited, the sanitizing time is shorter than that required for sanitizing the entire vehicle cabin.

The space sanitizing device may include at least one of a UV lamp that emits ultraviolet rays in the space, a sprayer that sprays a liquid disinfectant in the vehicle cabin, and an injector that injects a gaseous gas in the space. Note that the higher the concentration of the disinfectant, the higher the sanitizing effect, but the higher the concentration of the disinfectant, the more harmful it is to the human body. Therefore, when a high-concentration disinfectant is supplied to the vehicle cabin in the form of mist or gas, it is required that the taxi vehicle 12 be provided with a sufficient sealing mechanism to prevent the disinfectant from leaking to the outside of the vehicle. In addition, during the period while a high-concentration disinfectant is supplied to the vehicle cabin in the form of mist or gas, it is required that the ventilation processing, which replaces the vehicle cabin air with the outside air, not be performed and that the doors not be opened.

In the meantime, in such sanitization processing, the higher the strength of the cleaning energy and the higher the concentration of the disinfectant, the higher the sanitizing effect and the shorter the sanitization processing. However, high-intensity cleaning energy or a high-concentration disinfectant is often harmful to humans and animals. In addition, some materials are deteriorated and damaged depending upon the type of cleaning energy and disinfectants. For example, though ozone gas has a high sanitizing effect, it is known that high-concentration ozone gas deteriorates resin. Therefore, it is not desirable to perform sanitization processing with a person or a piece of baggage (including animals) still present in the vehicle cabin. To address this problem, before the sanitization processing, the vehicle controller 20 confirms the detection result of the presence sensor 36. If it is detected that, as a result of this confirmation, at least one of a person and a piece of baggage is still present in vehicle cabin, the vehicle controller 20 prohibits the sanitization processing. If the presence of a piece of baggage is detected, the vehicle controller 20 may send a message to the user terminal 110 to notify that the baggage is present in the vehicle cabin.

When a person outside the vehicle wishes to start using the taxi vehicle 12 while the sanitization processing is in progress, the cleaning device 38 finishes the sanitization processing even before the sanitization processing is completed so that the user 100 can ride on the vehicle. In this case, the payment device 42 may change the usage fare of the taxi vehicle 12 according to the degree of cleaning at the time when the user starts using the vehicle. That is, when the user starts using the vehicle in the state in which the cleaning is insufficient, the usage fare may be set lower than the usage fare when the user starts using the vehicle in the state in which the cleaning is completed.

To remove harmful materials and/or odors from the vehicle cabin, the cleaning device 38 may have an air replacement device that replaces the air in the vehicle cabin with clean air. The air replacement device may include at least one of a ventilation device and an air cleaner. The ventilation device is a device that replaces the air in the vehicle cabin with the air outside the vehicle. For example, the in-vehicle air conditioner, when operated in the outside air take-in mode, functions as a ventilation device. The air cleaner is a device that cleans the air in the vehicle cabin using a filter and then returns the cleaned air to the vehicle cabin. The use of such a ventilation device or an air cleaner makes it possible to clean the air in the vehicle. Since the taxi vehicle 12 in this example is a single-seater small vehicle and its cabin space is small, air can be replaced in about a few minutes. In addition, the cleaning device 38 may include a device that outputs an aromatic disinfectant to mask the odors with other good scents.

Figure 6:
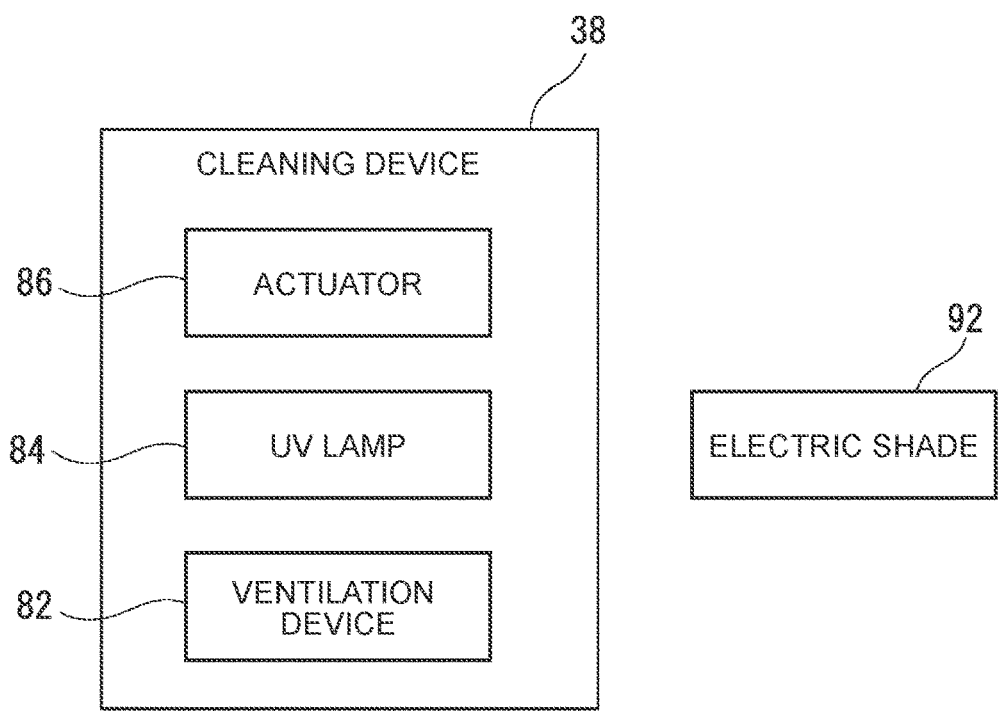
FIG. 6 is a diagram showing an example of a cleaning device.

Next, a specific example of the cleaning device 38 will be described. FIG. 6 is a diagram showing an example of the cleaning device 38. In the example in FIG. 6, the cleaning device 38 includes a UV lamp 84, an actuator 86, and a ventilation device 82. The UV lamp 84 emits ultraviolet rays, called "ultraviolet rays C", at a wavelength of 200 nm to 280 nm. Ultraviolet rays C, also called "bactericidal ultraviolet rays", are known to effectively inactivate bacteria and viruses that cause infectious diseases. For example, it is known that 99.9% of influenza virus is inactivated by applying ultraviolet rays C at an irradiation amount of equal to or higher than 6.6 mJ/cm$^2$.

Although ultraviolet rays C have a high sanitizing ability, a shaded portion where the ultraviolet rays C do not reach cannot be sanitized as a matter of course. Therefore, the cleaning device 38 shown in FIG. 6 has the actuator 86 that changes at least one of the orientation and the position of the UV lamp 84 according to an instruction from the vehicle controller 20. The actuator 86 includes, for example, a motor, an electromagnetic cylinder, and the like. Changing at least one of the position and orientation of the UV lamp 84 with the use of the actuator 86 allows ultraviolet rays to reach various parts of the vehicle cabin. In one taxi vehicle 12, there needs not be one UV lamp 84 and one actuator 86; instead, there may be a plurality of UV lamps 84 and a plurality of actuators 86. In the example in FIG. 6, space sanitization is performed using ultraviolet rays C to sanitize the entire space of the vehicle cabin.

Ultraviolet rays C have a high sanitizing ability but are harmful to the human body. Therefore, the use of ultraviolet rays C in the manned environment is prohibited. As repeatedly stated, the taxi vehicle 12 in this example is a driverless vehicle and, therefore, the taxi vehicle 12 is an unmanned vehicle after the user 100 get out of it. Therefore, in an unmanned vehicle, it is possible to apply ultraviolet rays C to the entire vehicle cabin. In addition, to prevent the light of the UV lamp 84 from leaking to the outside of the vehicle, the cleaning device 38 in this example has an electric shade 92. This electric shade 92 covers the windows to prevent the light of the UV lamp 84 from leaking to the outside of the vehicle. Before turning on the UV lamp 84, the vehicle controller 20 drives the electric shade 92 to cover the windows with the shade members. In addition, while the UV lamp 84 is turned on, the vehicle controller 20 locks the doors with the use of the door actuator 34 to prevent a person from getting in the vehicle. Furthermore, while it is detected by the presence sensor 36 that a person or a piece of baggage is still present in the vehicle, the vehicle controller 20 does not turn on the UV lamp 84.

The ventilation device 82, which replaces the vehicle cabin air with the outside air, is actually an in-vehicle air conditioner. This ventilation device 82 may be driven concurrently with the application of ultraviolet rays C. As a matter of course, an air cleaner may be provided in place of or in addition to the ventilation device 82. In any case, the cleaning device 38 in FIG. 6 sanitizes the entire space of the vehicle cabin using the UV lamp 84, making it possible to sanitize the vehicle cabin more thoroughly.

Figure 7:
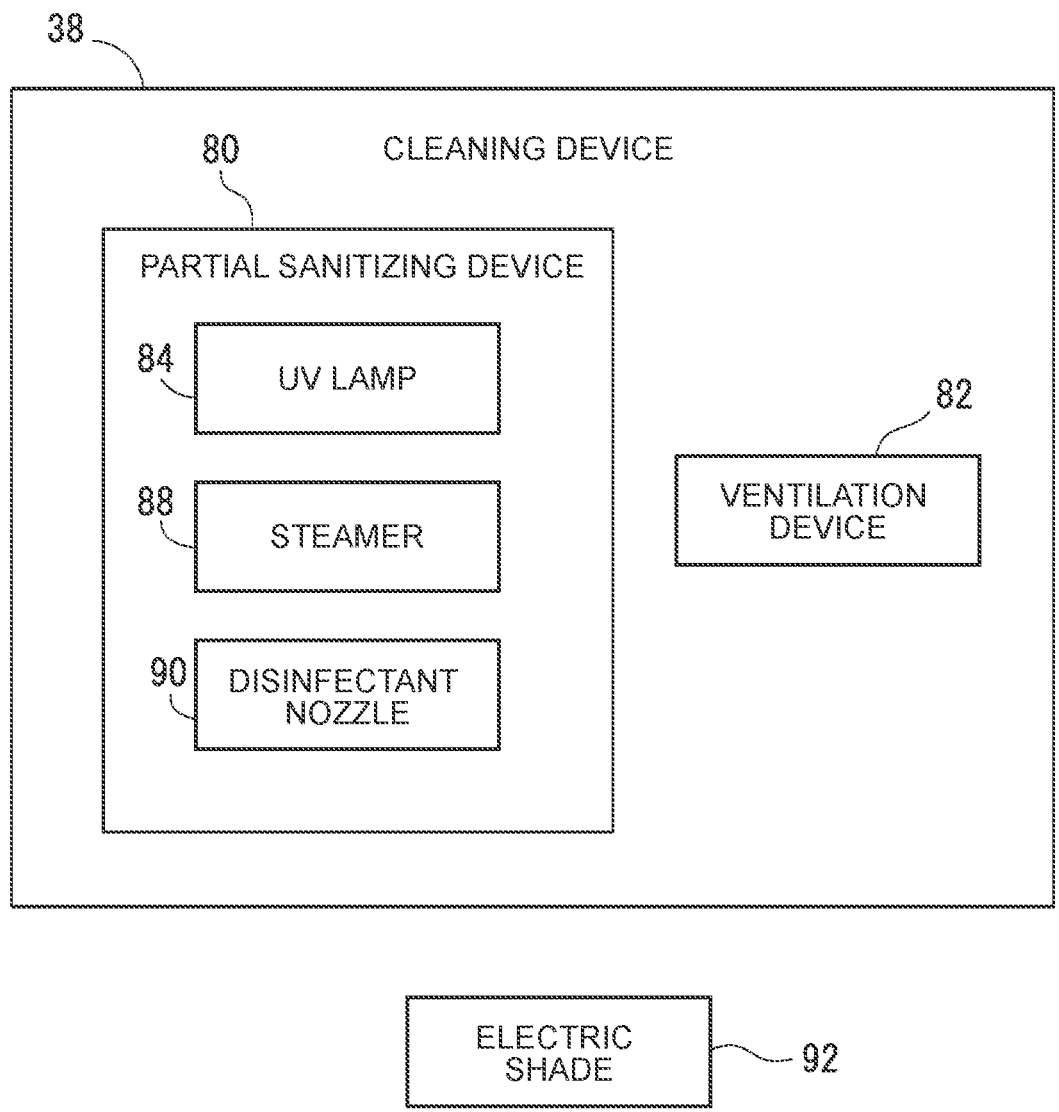
FIG. 7 is a diagram showing another example of a cleaning device.

Next, another example of the cleaning device 38 will be described. FIG. 7 is a block diagram showing another example of the cleaning device 38. This cleaning device 38 includes a partial sanitizing device 80 and the ventilation device 82. The ventilation device 82, a device that replaces the vehicle cabin air with the outside air as described above, is actually an in-vehicle air conditioner.

The partial sanitizing device 80 is a device that sanitizes the surface of a part where the fingers of the user 100 have touched. Finger-touched parts include, for example, an operation panel, a handle, a seat, etc. The partial sanitizing device 80 performs the surface sanitization processing for these finger-touched parts. The configuration of the partial sanitizing device 80 is not particularly limited. For example, the partial sanitizing device 80 may include at least one of the UV lamp 84 that emits ultraviolet rays C, a steamer 88 that injects steam, and a disinfectant nozzle 90 that ejects a liquid disinfectant. The partial sanitizing device 80 may change the content of the sanitization processing depending upon the characteristics of a sanitizing part. For example, when sanitizing the surface of an electronic component such as the operation panel, the partial sanitizing device 80 may use the UV lamp 84 or a highly volatile disinfectant (e.g., ethanol, etc.) for sanitization instead of using the steamer 88 or a moist disinfectant. Similarly, when sanitizing the surface of a member made of resin such as a handle, the partial sanitizing device 80 may use the steamer 88 or disinfectants, which do not deteriorate resin, instead of using the UV lamp 84.

The electric shade 92 should be driven to cover the windows also when ultraviolet rays C are used for partial sanitization. In addition, when the presence sensor 36 detects the presence of at least one of a person or a piece of baggage in the vehicle cabin, the vehicle controller 20 does not drive the partial sanitizing device 80.

When only a part where the fingers of the user 100 have touched is sanitized as shown in the example in FIG. 7 instead of sanitizing the entire vehicle cabin, the sanitization time is much shorter than that required for sanitizing the entire space of the vehicle cabin. Nevertheless, sanitizing a part where the fingers of the user 100 have touched and ventilating the vehicle cabin can sufficiently reduce the risk of infection with infectious diseases.

The configurations of the cleaning device 38 shown in FIG. 6 and FIG. 7 are examples only and may be changed as appropriate. For example, though ultraviolet rays C are used in FIG. 6 to sanitize the vehicle cabin space, other disinfectants such as ozone gas and hypochlorous acid water may also be used. The configuration of the partial sanitizing device may also be changed as appropriate.

Figure 8:
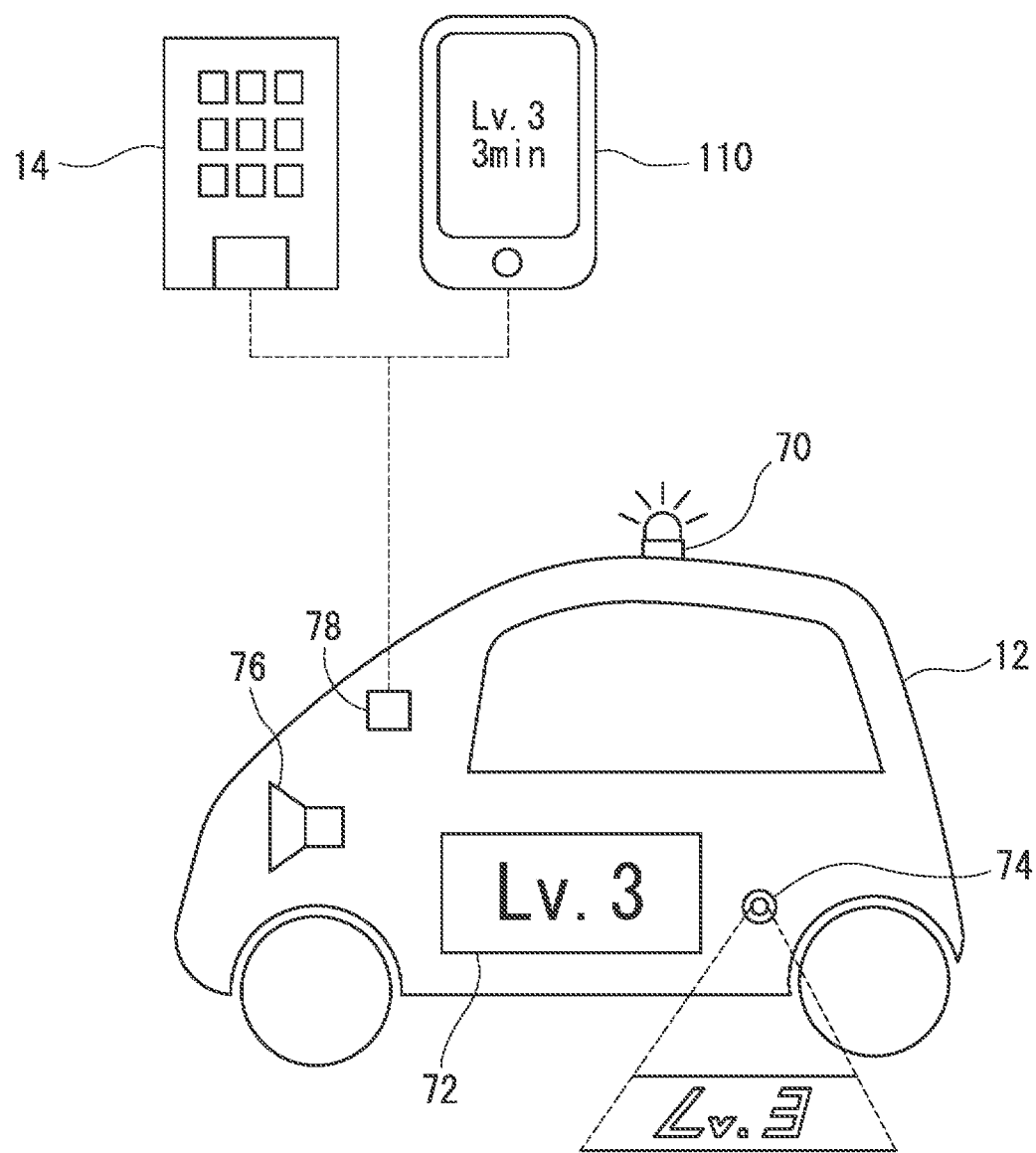
FIG. 8 is an image diagram showing a configuration of a notification device.

Next, the configuration of the notification device 40 will be described. FIG. 8 is an image diagram showing the configuration of the notification device 40. As described above, the notification device 40 is a device that notifies persons outside the vehicle of the cleaning level of the taxi vehicle 12. The cleaning level is a numerical value indicating the cleaning degree of the vehicle cabin, for example, a numerical value indicating the progress of the cleaning processing. In the example in FIG. 8, the cleaning level is set in the range of Lv. 0-Lv. 5. The numerical value of the cleaning level is incremented by one each time the cleaning processing advances by 20% and, when the cleaning processing is completely finished, the cleaning level becomes Lv. 5.

The notification device 40 notifies persons outside the vehicle of this cleaning level. For use in this notification, the notification device 40 may have a notification light 70. The notification light 70 is attached to the taxi vehicle 12, for example, at a position visible from outside of the vehicle (for example, on the ceiling of the taxi vehicle 12). In this case, the color and the lighting form of the notification light 70 may be changed according to the cleaning level to notify the surrounding persons of the cleaning level.

As another form, the notification device 40 may have a display 72. This display 72 displays an image in the display area that is set at a position on the taxi vehicle 12 and is visible from outside of the vehicle (for example, on the side surface of the taxi vehicle 12). As a still another form, the notification device 40 may have a projector 74 that projects an image onto the road surface around the taxi vehicle 12. In this case, the display 72 or the projector 74 may display or project an image indicating the cleaning level. In addition to the image indicating the cleaning level, an image indicating the estimated time required to completely finish the cleaning processing may also be displayed or projected.

As a still another form, the notification device 40 may have a speaker 76 that outputs a voice to the outside of the taxi vehicle 12. In this case, the speaker 76 may output at least a voice indicating the cleaning level and may further output an estimated time required to finish the cleaning processing completely. As a still another form, the notification device 40 may have a communication device 78 that sends the cleaning level to the user terminals 110 that are around the taxi vehicle 12.

The notification device 40, when provided in this way, allows those who are around the taxi vehicle 12 and wish to use it, that is, those who wish to pick up the taxi vehicle 12 in pickup usage mode, to know the cleaning degree of the taxi vehicle 12 without having to ride on it. This can greatly reduce anxiety of the user 100 about sanitation when using the taxi vehicle 12.

In this example, even when the cleaning processing is not completely finished, the user 100 can start using the taxi vehicle 12 as mentioned above if so desired by the user 100. That is, in the pickup usage mode, when the user 100 notifies the taxi vehicle 12 of an intention to start using it, the taxi vehicle 12 finishes the sanitization processing and allows user 100 to start using it. In this case, the taxi vehicle 12 offers a usage fare lower than that to be offered when the user 100 starts using the taxi vehicle 12 after the cleaning processing is completed. This configuration allows the user 100 in a hurry to start using the taxi vehicle 12 immediately. In addition, the taxi vehicle 12 improves its profitability since the waiting time, during which the taxi vehicle 12 is not transporting the user 100, is reduced.

In the description above, the notification device 40 notifies those who are around the taxi vehicle 12, that is, those who are trying to pick up the taxi vehicle 12, of the cleaning level. However, the notification device 40 may also notify those who are away from the taxi vehicle 12, that is, those who are trying to use the taxi vehicle 12 in the calling usage mode, of the cleaning level.

Figure 9:
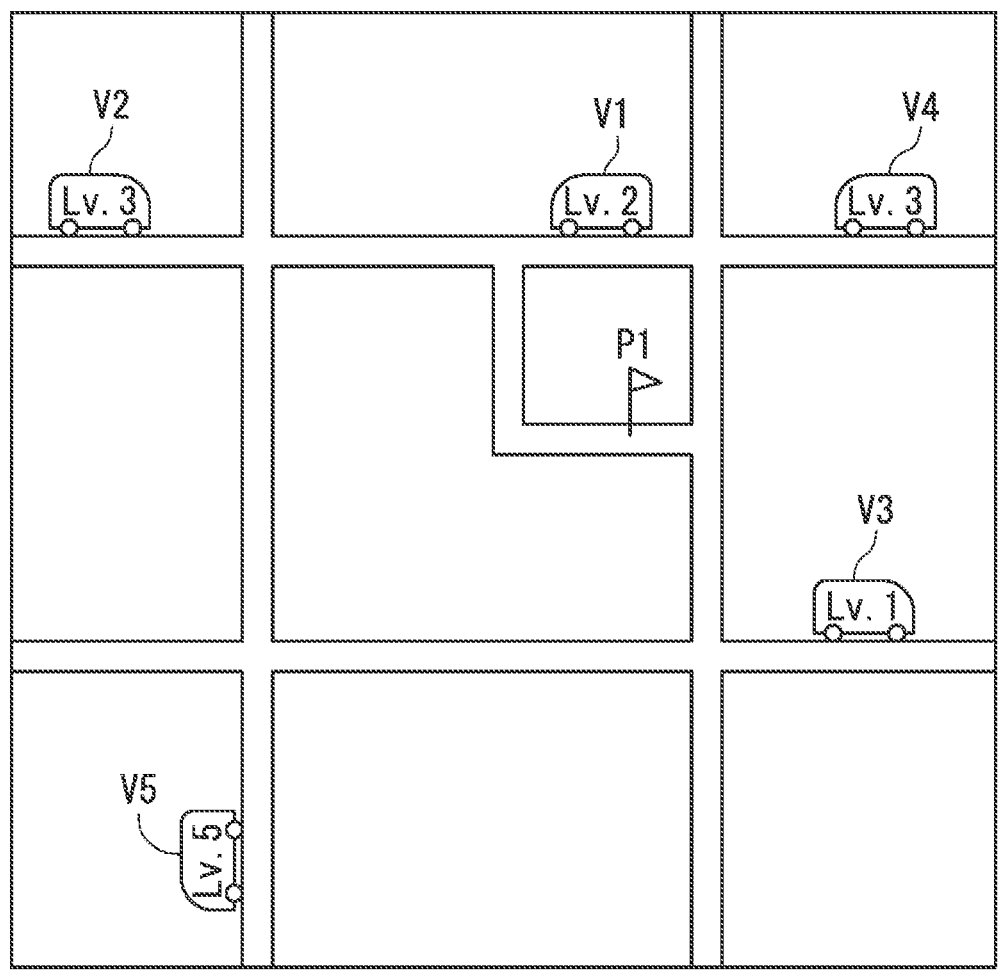
FIG. 9 is a diagram showing an example of an image displayed on a user terminal based on a vehicle list.

For example, as shown in FIG. 2, the user 100 sends the usage request 64 to the management device 14 in the calling usage mode to call the taxi vehicle 12 as described above. Upon receiving the usage request 64, the management device 14 sends a list of taxi vehicles 12 available to user 100, that is, the vehicle list 66, to the user terminal 110. In this case, along with the vehicle list 66, the management device 14 also sends the information on the cleaning level of each of the taxi vehicles 12 to the user terminal 110. The user terminal 110 displays the received information on the screen. FIG. 9 is a diagram showing an example of an image displayed on the user terminal 110 based on the vehicle list 66. In the example in FIG. 9, mark P1, which indicates the current position, and marks V1 to V5, which indicate the available taxi vehicles 12, are superimposed on the map image around the user 100. Marks V1 to V5 indicating the taxi vehicles 12 also include an image indicating the current cleaning level of the taxi vehicle 12. The user 100 views this image, displayed on the user terminal 110, and selects the taxi vehicle 12 that he or she wants to call.

For example, when the cleaning level is low but the user 100 wishes to use the taxi vehicle 12 immediately, the user 100 may select mark V1 of the taxi vehicle 12 that is nearest to the user 100. On the other hand, when more emphasis is on sanitation, the user 100 may select mark V5 of the taxi vehicle 12 that is a little away but has a high cleaning level. In this way, by notifying the user 100 of the cleaning level of each of the taxi vehicle 12, the user 100 can select the taxi vehicle 12 that suits his/her wishes.

In addition to the cleaning level, the notification device 40 may notify about whether smoking is permitted in the taxi vehicle 12. That is, the taxi system 10, which has a plurality of the taxi vehicles 12, may divide the taxi vehicles 12 into non-smoking vehicles in which smoking is prohibited and smoking vehicles in which smoking is permitted. Then, via the notification device 40, each of the taxi vehicles 12 may notify persons outside the vehicle who wish to use the vehicle about whether smoking is permitted. This configuration allows both smokers and non-smokers to selectively use the taxi vehicle 12 and to use the taxi vehicle 12 more comfortably.

The configurations described above are all examples. The requirements for the configuration of the taxi vehicle 12 are that (1) the taxi vehicle 12 includes the cleaning device 38 that performs cleaning processing after the end of use by the user 100 and the notification device 40 that notifies those outside the vehicle who wish to use the vehicle of the cleaning degree of the vehicle cabin and (2) the taxi vehicle 12 transports a user to the destination autonomously with no driver in the vehicle. As long as these requirements are met, other configurations may be modified. For example, the taxi vehicle 12, though a single-seater in this example, may be a multi-seater as long as the taxi vehicle 12 becomes unmanned after the end of use.

What is claimed is:

1. A taxi vehicle that autonomously transports a user to a destination with no driver in the vehicle, the taxi vehicle comprising:

a cleaning device configured to perform sanitization processing for removing at least one of harmful materials and odors from a vehicle cabin after the user has finished using the taxi vehicle, the harmful materials being harmful to a human body;

a notification device configured to notify a person of a cleaning degree of the vehicle cabin, the person being a person outside the vehicle who wishes to use the vehicle; and a vehicle controller, wherein the cleaning device includes an entire space sanitizing device that is an ultraviolet-ray lamp (UV lamp), a partial sanitizing device that is a disinfectant nozzle, and a ventilation device that is an in-vehicle air conditioner, the UV lamp is configured to emit ultraviolet rays at a wavelength of 200 nm to 280 nm and at an irradiation amount of equal to or higher than 6.6 mJ/cm$^2$, the disinfectant nozzle is configured to supply a mist or gas disinfectant that does not deteriorate resin, and the vehicle controller is configured to cause the UV lamp to emit the ultraviolet rays and drive the in-vehicle air conditioner at a same time, and cause the disinfectant nozzle to supply the mist or gas disinfectant and stop the in-vehicle air conditioner at a same time.

2. The taxi vehicle according to claim 1, further comprising a presence sensor configured to detect whether a person or a piece of baggage is still present in the vehicle cabin, wherein the cleaning device is configured not to perform the sanitization processing during a period while the presence sensor detects that at least one of the person and the baggage is still present in the vehicle cabin.

3. The taxi vehicle according to claim 1, further comprising a payment device configured to be used for paying a usage fare of the taxi vehicle, wherein:

when the user starts using the taxi vehicle, the cleaning device is configured to finish the sanitization processing even before the sanitization processing is completed; and the payment device is configured to change the usage fare according to a cleaning degree at a time when the user starts using the taxi vehicle.

4. The taxi vehicle according to claim 1, wherein the notification device includes at least one of a light, a display, a projector, a speaker, and a communication device, the light being installed at a position that is on the taxi vehicle and is visible from outside of the taxi vehicle, the display being configured to display an image in a display area that is provided at a position on the taxi vehicle and is visible from outside of the taxi vehicle, the projector being configured to project an image on a road surface around the taxi vehicle, the speaker being configured to output a voice to the outside of the vehicle, the communication device being configured to send information to an information terminal outside the vehicle.

5. A taxi system including a plurality of the taxi vehicles according to claim 1, wherein:

the taxi vehicles are divided into smoking vehicles in which smoking is permitted and non-smoking vehicles in which smoking is prohibited; and the notification device is configured to output the cleaning degree and, in addition, whether smoking is permitted.

6. The taxi vehicle according to claim 1, wherein:

the cleaning device further includes an actuator connected to the UV lamp, and the vehicle controller is configured to change at least one of an orientation or a position of the actuator to sanitize an entire space of the vehicle cabin.

7. The taxi vehicle according to claim 6, wherein the cleaning device includes a plurality of the UV lamps and a plurality of the actuators.

8. The taxi vehicle according to claim 1, wherein the partial sanitizing device is configured to sanitize a surface of a part where fingers of the user have touched.

9. The taxi vehicle according to claim 8, wherein the disinfectant nozzle is configured to supply the mist or gas disinfectant to surfaces of an operation panel, a handle and a seat in the vehicle cabin.

* * * * *